(12) United States Patent
Charlton

(10) Patent No.: US 6,958,052 B1
(45) Date of Patent: Oct. 25, 2005

(54) ESOPHAGEAL BALLOON CATHETER

(76) Inventor: Nicola Charlton, 13209 Hawthorne Ct., Mequon, WI (US) 53097

( * ) Notice: Subject to any disclaimer, the term of this patent is extended or adjusted under 35 U.S.C. 154(b) by 513 days.

(21) Appl. No.: 09/947,943

(22) Filed: Sep. 5, 2001

Related U.S. Application Data

(60) Provisional application No. 60/230,076, filed on Sep. 5, 2000.

(51) Int. Cl.[7] ............................................. A61M 29/00
(52) U.S. Cl. .................. 604/102.02; 604/915
(58) Field of Search ................... 604/93.01, 96.01, 604/101.03, 102.03, 103.01, 264, 275, 270, 604/910, 902, 915, 102.01–102.02; 606/192, 606/196

(56) References Cited

U.S. PATENT DOCUMENTS

| | | | |
|---|---|---|---|
| 4,367,747 A | 1/1983 | Witzel | 128/344 |
| 4,453,545 A | 6/1984 | Inoue | 128/207.1 |
| 4,729,384 A | 3/1988 | Bazenet | 128/691 |
| 4,752,286 A | 6/1988 | Okada | 604/96 |
| 5,263,485 A | 11/1993 | Hickey | 128/673 |
| 5,314,409 A * | 5/1994 | Sarosiek et al. | 604/101.03 |
| 5,398,692 A | 3/1995 | Hickey | 128/673 |
| 5,681,344 A | 10/1997 | Kelly | 606/194 |
| 5,785,684 A | 7/1998 | Zimmon | 604/96 |
| 5,904,648 A | 5/1999 | Arndt et al. | 600/120 |
| 5,947,926 A | 9/1999 | Zimmon | 604/96 |

* cited by examiner

Primary Examiner—LoAn H. Thanh

(57) ABSTRACT

An esophageal balloon catheter capable of quickly and safely providing esophageal gauging and stenting as well as gastric aspiration during esophageal surgery. The esophageal balloon catheter includes (i) a shaft which defines a gastric lumen and an inflation lumen, (ii) a single inflatable balloon sealingly attached to the shaft at a fixed longitudinal position proximate the distal end of the shaft in fluid communication with the inflation lumen, and (iii) an aspiration port through the shaft between the balloon and the distal end of the shaft in fluid communication with the gastric lumen. The gastric lumen is not in fluid communication with the inflation lumen or the balloon so as to allow aspiration of the stomach without causing inflation or deflation of the balloon.

9 Claims, 2 Drawing Sheets

ESOPHAGEAL BALLOON CATHETER

This application claims the benefit of Provisional Application Ser. No. 60/230,076, filed Sep. 5, 2000.

FIELD OF THE INVENTION

The invention relates to catheters. More specifically, the invention relates to esophageal catheters.

BACKGROUND

Esophageal surgery, such as esophageal diverticulectomy, Nissen fundo plication, and anti-reflux procedures, carry a risk of narrowing the esophagus resulting in difficulty swallowing. Such narrowing can be prevented by stenting the esophagus during surgery. Stenting of the esophagus is currently achieved by placing a lead or mercury filled esophageal dilator within the esophagus during surgery. Such lead dilators are cumbersome, and increase the risk of esophageal injury and esophageal perforation.

In order to allow aspiration of the stomach during esophageal surgery, a gastric tube is typical placed down the esophagus and into the stomach at the start of surgery. Unfortunately, the presence of both an esophageal dilator and a gastric tube within the esophagus can hamper the surgical procedure, particularly when one or the other of the esophageal dilator and gastric tube need to be changed or repositioned during surgery.

Accordingly, a need exists for a medical device capable of quickly and safely providing esophageal gauging and stenting as well as gastric aspiration during esophageal surgery.

SUMMARY OF THE INVENTION

The invention is an esophageal balloon catheter capable of quickly and safely providing esophageal gauging and stenting as well as gastric aspiration during esophageal surgery. The esophageal balloon catheter includes (i) a shaft which defines a gastric lumen and an inflation lumen, (ii) a single inflatable balloon sealingly attached to the shaft at a fixed longitudinal position proximate the distal end of the shaft in fluid communication with the inflation lumen, and (iii) an aspiration port through the shaft between the balloon and the distal end of the shaft in fluid communication with the gastric lumen. The gastric lumen is not in fluid communication with the inflation lumen or the balloon so as to allow aspiration of the stomach without causing inflation or deflation of the balloon.

The esophageal balloon catheter may be used to stent the esophagus of a patient during surgery while allowing aspiration of the stomach through the stent by (i) obtaining an esophageal balloon catheter as described above, (ii) introducing the esophageal balloon catheter into the esophagus of the patient a distance sufficient to position the balloon along the length of the esophagus to be stented, (iii) inflating the balloon through the inflation lumen, (iv) aspirating the patient's stomach through the gastric lumen, (v) performing a surgical procedure on the patient, (vi) deflating the balloon, through the inflation lumen, and (vii) removing the esophageal balloon catheter from the esophagus of the patient.

DETAILED DESCRIPTION OF THE INVENTION INCLUDING A BEST MODE

Figure 1:
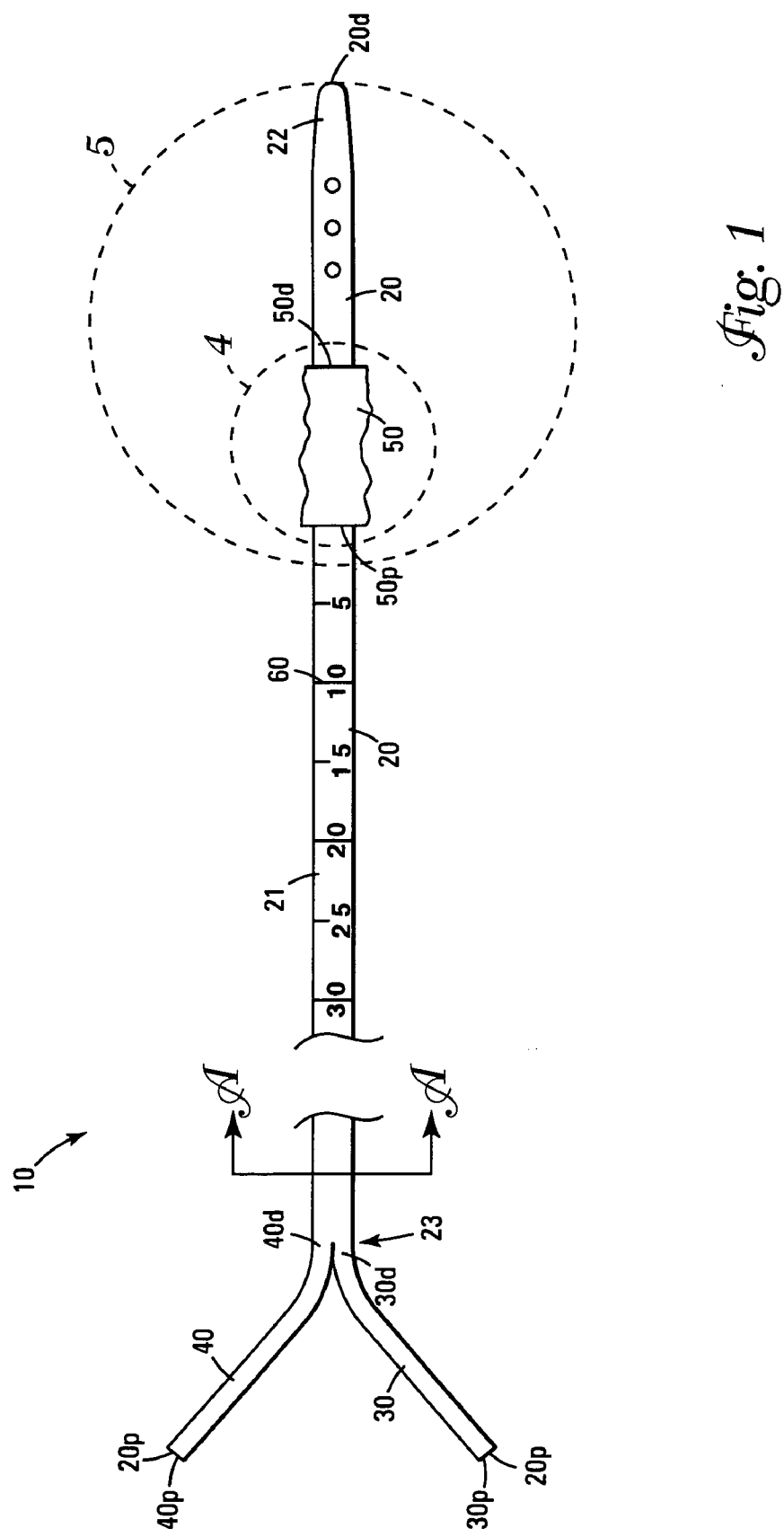
FIG. 1 is a side view of one embodiment of the esophageal balloon catheter of this invention.

Nomenclature
   10 Esophageal Balloon Catheter
   20 Shaft
   20d Distal End of Shaft
   20p Proximal End of Shaft
   21 Exterior Surface of Shaft
   22 Tip of Shaft
   23 Bifurcation Point on Shaft
   28 Gastric Lumen
   28a Aspiration Port
   29 Inflation Lumen
   29a Inflation Port
   30 Gastric Tube
   30d Distal End of Gastric Tube
   30p Proximal End of Gastric Tube
   40 Inflation Tube
   40d Distal End of Inflation Tube
   40p Proximal End of Inflation Tube
   50 Balloon
   50d Distal End of Balloon
   50p Proximal End of Balloon
   59 Balloon Lumen
   60 Distance Markings Construction The invention is an esophageal balloon catheter 10 which includes a longitudinally elongated shaft 20 defining a gastric lumen 28 and an inflation lumen 29, and a single inflatable balloon 50 sealingly attached to the shaft 20 at a fixed longitudinal position proximate the distal end 20d of the shaft 20.

The single balloon 50 is in fluid communication with the inflation lumen 29 via an inflation port 29a through the shaft 20. The gastric lumen 28 exits the shaft 20 at an aspiration port 28a located between the balloon 50 and the distal end 20d of the shaft 20. The gastric lumen 28 and inflation lumen 29 are maintained as separate and individual lumens 28 and 29 so that the gastric lumen 28 is not directly or indirectly in fluid communication with the balloon 50 and the inflation lumen 29 is not directly or indirectly in fluid communication with the aspiration port 28a.

Figure 2:
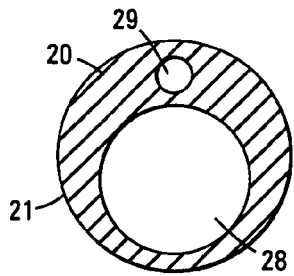
FIG. 2 is an enlarged cross-sectional view of the esophageal balloon catheter of FIG. 1 taken along line A—A.
Figure 3:
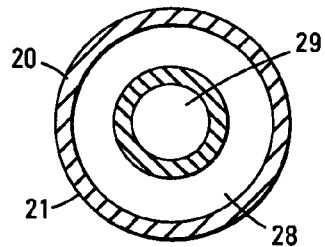
FIG. 3 is an enlarged cross-sectional view of a second embodiment of an esophageal balloon catheter.
Figure 4:
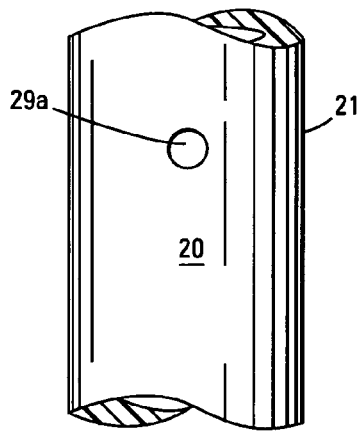
FIG. 4 is an enlarged top view of a section of the esophageal balloon of FIG. 1 encompassed by circle B with the balloon removed to facilitate viewing of the inflation port.

One embodiment of the esophageal balloon catheter 10 is a Nissen esophageal balloon catheter 10 as shown in FIG. 1. The elongated flexible shaft 20 defines a gastric lumen 28 and an inflation lumen 29. The lumens 28 and 29 may be configured as coaxial lumens 28 and 29 such as shown in FIG. 3, but are preferably configured as dual side-by-side lumens 28 and 29 as shown in FIG. 2.

The shaft 20 preferably has a circular cross-sectional shape, but may be constructed with other shapes including specifically, but not exclusively oval, egg, and tear drop. The shaft 20 preferably has a circular cross-section of between about 10 to 20 French.

The elongated flexible shaft 20 has a distal end 20d and a proximal end 20p. The distal end 20d of the shaft 20 preferably has a rounded and tapered tip 22 to facilitate introduction of the catheter 10 into the esophagus (not shown) of a patient (not shown). The proximal end 20p of the esophageal balloon catheter 10 is preferably bifurcated at a bifurcation point 23 into a gastric tube 30 continuing the gastric lumen 28 and an inflation tube 40 continuing the inflation lumen 29. Bifurcation of the shaft 20 and the lumens 28 and 29 allows the lumens 28 and 29 to be individually connected to separate pieces of equipment utilizing standard connectors.

The shaft 20 preferably has the lengths set forth below in Table One.

TABLE ONE

| END POINTS | | LENGTH GENERAL (cm) | PREFERRED (cm) |
|---|---|---|---|
| Distal End of Shaft 20d | Proximal End of Shaft 20p | 70–260 | 100–220 |
| Distal End of Gastric Tube 30d | Proximal End of Gastric Tube 30p | 10–100 | 20–50 |
| Distal End of Inflation Tube 40d | Proximal End of Inflation Tube 40p | 10–100 | 20–50 |
| Distal End of Shaft 20d | Bifurcation Point 23 | 60–160 | 80–120 |
| Proximal End of Balloon 50p | Bifurcation Point 23 | 40–150 | 60–110 |
| Distal End of Balloon 50d | Proximal End of Balloon 50p | 3–20 | 4–10 |
| Distal End of Shaft 20d | Distal End of Balloon 50d | 3–20 | 4–10 |

The shaft 20 may be constructed from any of the well-known and widely recognized flexible, chemically inert and non-toxic materials from which the shaft of an esophageal catheter may be constructed, including specifically, but not exclusively polyvinyl chloride.

The gastric lumen 28 is intended to be used for aspirating the stomach (not shown) of a patient (not shown) once the balloon 50 has been properly positioned and inflated within the esophagus (not shown) of the patient (not shown). Accordingly, the gastric lumen 28 is preferably between about 5 to 15 French. The inflation lumen 29 is intended to be used for inflating the balloon 50 once the balloon 50 has been properly positioned within the esophagus (not shown) of the patient (not shown) in order to prevent the esophagus (not shown) from sealing shut during surgery, and for deflating the balloon 50 once surgery is complete so as to allow retraction and removal of the catheter 10 from the esophagus (not shown). Accordingly, the inflation lumen 29 is preferably between about 5 to 10 French.

An inflatable balloon 50 is sealingly connected to the shaft 20 at a fixed longitudinal position proximate the distal end 20d of the shaft 20. The longitudinal ends 50d and 50p of the balloon 50 may be sealingly and fixedly attached to the shaft 20 by any suitable means, such as a silicone adhesive bonding the longitudinal ends 50d and 50p of the balloon 50 to the exterior surface 21 of the shaft 20. The balloon 50 may be constructed from any of the well-known and widely recognized chemically inert and non-toxic materials from which the inflatable balloon of an esophageal catheter may be constructed, including thin films of low density polyethylene, polyethylene terephthalate, and polyurethane. The inflation lumen 29 extends through the wall (unnumbered) of the shaft 20 within the lumen 59 of the balloon 50 and forms an inflation port 29a. This allows the balloon 50 to be inflated and deflated through the inflation lumen 29 without effecting aspiration of the stomach (not shown).

The distal end 20d of the shaft 20 protrudes a distance beyond the balloon 50. The gastric lumen 28 is continued beyond the balloon 50 within the protruding distal end 20d of the shaft 20 and extends through the wall (unnumbered) of the shaft 20 between the balloon 50 and the distal end 20d of the shaft 20 to form at least one and preferably a plurality of aspiration ports 28a. This allows the stomach (not shown) of the patient (not shown) to be aspirated through the gastric lumen 28 without effecting inflation or deflation of the balloon 50.

The shaft 20 is inserted through the nasal passage (not shown), past the pharynx (not shown) and into the esophagus (not shown) of a patient (not shown) during esophageal surgery. The shaft 20 may optionally be inserted through the mouth (not shown). In order to facilitate proper longitudinal placement of the balloon 50 within the esophagus (not shown) of the patient (not shown) the shaft 20 is preferably printed with distance markings 60 at least about every 10 cm from the distal end 50d, proximal end 50p or center (unnumbered) of the balloon 50.

In a preferred embodiment, the balloon 50 is preferably (i) shaped as a cylinder with a capacity of about 1 to 5 milliliters, preferably about 2 to 3 milliliters, (ii) approximately 3 to 20 cm in length (i.e., distance from the distal end 50d of the balloon 50 to the proximal end 50p of the balloon 50), and (iii) defines a balloon lumen 59 having a diameter of about 30 to 50 French when fully inflated. Balloons 50 having larger and smaller dimensions are also contemplated by this invention and are therefore within the scope of the invention. The balloon 50 can be inflated to a predetermined diameter (unnumbered) with the introduction of a predetermined quantity of a fluid, such as air or saline, through the inflation lumen 29.

Use

Figure 5:
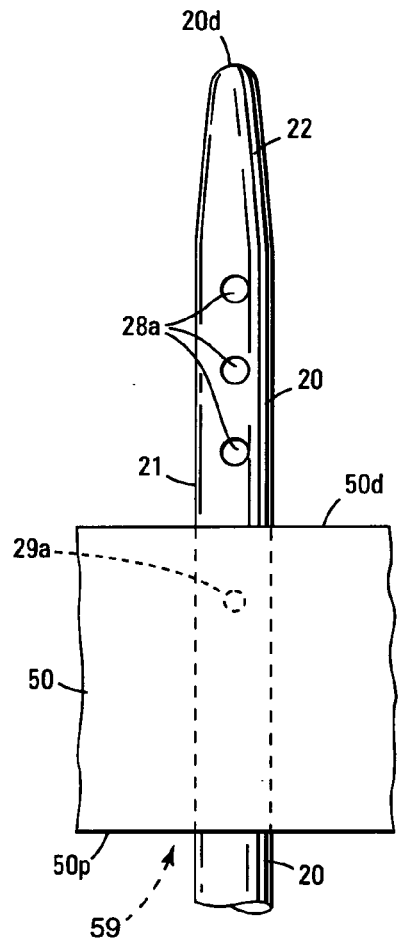
FIG. 5 is an enlarged top view of a section of the esophageal balloon of FIG. 1 encompassed by circle C with an inflated esophageal balloon.

Prior to introduction of the esophageal balloon catheter 10 in the esophagus (not shown) of a patient (not shown) the patient needs to prepare for surgery and placed under proper anesthetic. Once the patient has been anesthetized, the esophageal balloon catheter 10 is introduced into the patient's esophagus (not shown) through the oral cavity (not shown) using the distance markings 60 provided along the length of the shaft 20 to gauge proper positioning of the balloon 50 within the esophagus (not shown). Once the balloon 50 is positioned within the esophagus (not shown) at the location to be stented, a predetermined quantity of a pressurized fluid (not shown), such as a gas (not shown) or liquid (not shown), is injected into the balloon 50 through the inflation lumen 29 causing the balloon 50 to inflate as best shown in FIG. 5. When properly inflated, the balloon 50 will stent the esophagus (not shown) and thereby prevents narrowing of the esophagus (not shown). Should it be necessary, the balloon 50 can be deflated and reinflated any number of times while positioned within the esophagus (not shown) to gauge the size of the esophagus (not shown) or reposition the balloon 50.

The distal end 20d of the shaft 20 extends beyond the balloon 50 and into the stomach (not shown) of the patient (not shown) so as to place the aspiration port(s) 28a and thereby the gastric lumen 28 into fluid communication with the stomach of the patient (not shown). This allows aspiration of the patient's stomach (not shown) during surgery through the gastric lumen 28 despite the sealing effect of the inflated balloon 50 within the esophagus (not shown). Following completion of the surgical procedure, the balloon 50 is deflated and the esophageal balloon catheter 10 is removed from the esophagus (not shown) of the patient (not shown).

What is claimed is:

1. An esophageal balloon catheter, comprising:
   (a) a shaft having a proximal end, a distal end and a longitudinal length, and defining a gastric lumen and an inflation lumen;
   (b) a single inflatable balloon, the inflatable balloon sealingly attached to the shaft at a fixed longitudinal position proximate the distal end of the shaft in fluid communication with the inflation lumen; and
   (c) an aspiration port through the shaft between the balloon and the distal end of the shaft in fluid communication with the gastric lumen;
   (d) wherein the gastric lumen is not in fluid communication with the inflation lumen or the balloon.

2. The esophageal balloon catheter of claim 1 wherein the shaft has a circular cross-section of between about 10 to 20 French.

3. The esophageal balloon catheter of claim 1 wherein the gastric lumen is between about 5 to 15 French.

4. The esophageal balloon catheter of claim 1 wherein the inflation lumen is between about 5 to 10 French.

5. The esophageal balloon catheter of claim 1 comprising a plurality of aspiration ports through the shaft between the balloon and the distal end of the shaft in fluid communication with the gastric lumen.

6. The esophageal balloon catheter of claim 1 wherein the gastric lumen and inflation lumen are configured and arranged as dual side-by-side lumens.

7. The esophageal balloon catheter of claim 1 further comprising distance markings along the exterior surface of the shaft indicating distance from the balloon towards the proximal end of the shaft.

8. The esophageal balloon catheter of claim 1 wherein the shaft bifurcates proximate the proximal end of the shaft into separate and independent tubes with a first tube continuing the gastric lumen only and a second tube continuing the inflation lumen only.

9. The esophageal catheter of claim 2 wherein the distance markings appear at least every 10 cm with a numerical indication of the distance from the balloon.

* * * * *